United States Patent [19]

Herbstman et al.

[11] 4,138,444

[45] Feb. 6, 1979

[54] SELF-ALKYLATION OF ISOBUTANE

[75] Inventors: Sheldon Herbstman, Spring Valley; Edward L. Cole, Fishkill; John H. Estes, Wappingers Falls, all of N.Y.

[73] Assignee: Texaco Inc., New York, N.Y.

[21] Appl. No.: 848,186

[22] Filed: Nov. 3, 1977

[51] Int. Cl.$^2$ ................................................ C07C 3/56
[52] U.S. Cl. .......................... 260/683.47; 260/683.68
[58] Field of Search ...................... 260/683.47, 683.68, 260/683.4 R, 683.43

[56] References Cited

U.S. PATENT DOCUMENTS

| | | | |
|---|---|---|---|
| 2,361,755 | 10/1944 | Fawcett et al. | 260/683.4 R |
| 2,404,483 | 7/1946 | Frey | 260/683.4 R |
| 3,239,577 | 3/1966 | Bloch et al. | 260/683.47 |
| 3,523,142 | 8/1970 | Mih et al. | 260/683.47 |
| 3,549,718 | 12/1970 | Estes et al. | 260/683.47 |
| 4,066,716 | 1/1978 | Herbstman et al. | 260/683.47 |

*Primary Examiner*—George Crasanakis
*Attorney, Agent, or Firm*—Thomas H. Whaley; Carl G. Ries; George J. Darsa

[57] ABSTRACT

Isobutane is self-alkylated to an alkylate composition having high octane components including trimethylpentanes in the presence of a solid catalyst and a minor amount of a $C_5$ and higher olefin. The self-alkylation process utilizes a chlorided alumina catalyst having from about 4 to 15 weight percent chlorine. The olefins of choice employed in the isobutane self-alkylation reaction are isoolefins having 6 or 7 carbons. The isobutane may be derived from the isomerization of n-butane and the isomerization process may be integrated with the self-alkylation process.

25 Claims, No Drawings

SELF-ALKYLATION OF ISOBUTANE

BACKGROUND OF THE INVENTION

The reaction involving the combination of two moles of isobutane has been previously reported, for example, in the Journal of Organic Chemistry, 6, 647 (1941) and 29 (6), 1497 (1964). This abnormal reaction of isobutane with certain olefins has become known as self-alkylation or hydrogen transfer. The overall reaction involving isobutane and $C_5$ or higher olefins results in the production of a branched octane and a paraffin corresponding in carbon content to the olefin employed as follows:

$$2\ i\text{-}C_4H_{10} + C_nH_{2n} \rightarrow i\text{-}C_8H_{18} + C_nH_{2n+2}$$

The self-alkylation referred to above is distinguishable from direct alkylation of an isoparaffin, and in the typical instance, with a normal $C_2$ to $C_4$ olefin. In direct alkylation the number of carbons in the product correspond to the sum of the carbons of the isoparaffin and olefin reactants. For example, the direct alkylation of isobutane and ethylene forms a $C_6$ isomer, such as 2,3-dimethylbutane, as follows:

$$i\text{-}C_4H_{10} + C_2H_4 \rightarrow i\text{-}C_6H_{14}$$

With respect to the self-alkylation reaction, the ionic reaction involving hydrogen transfer has been conducted in the presence of an acid catalyst, typically concentrated (95+ weight percent) sulfuric acid. While sulfuric acid is extremely effective as a catalyst in self-alkylation reactions, the acid presents substantial problems from the standpoint of safety and the cost of equipment in view of the highly corrosive nature of this material. In addition to the disadvantages associated with the use of an acid catalyst in the process, there exists problems in the disposal of such waste products as sulfuric acid sludge. Further, the use of a liquid acid catalyst requires that the same be recovered from the reaction by air burning and reconstitution which additionally presents problems of safety along with meeting environmental requirements necessitating the use of costly equipment.

It is therefore an object of this invention to provide a process for the self-alkylation of isobutane which can be undertaken in the presence of a solid catalyst.

Another object of this invention is to provide a process for the self-alkylation of isobutane which avoids the use of highly corrosive materials.

Yet another object of this invention is to provide a process for the self-alkylation of isobutane which does not entail disposal of corrosive waste products.

A further object of this invention is to provide a combined isomerization and self-alkylation process wherein n-butane is converted to high octane components.

Other objects and advantages will become apparent from a reading of the following detailed description and examples.

SUMMARY OF THE INVENTION

Broadly, this invention contemplates a process for the self-alkylation of isobutane which comprises contacting isobutane and a $C_5$ and higher olefin under self-alkylation conditions with a solid catalyst comprising chlorided alumina. The chlorided alumina contemplated as the solid catalyst in the self-alkylation reaction comprises eta or gamma alumina, preferably gamma alumina, and from about 4 to 15 weight percent chlorine.

We have found that the self-alkylation reaction described herein can be undertaken in the presence of a solid catalyst composed of eta or gamma alumina and from about 4 to 15 weight percent chlorine, preferably from about 7 to 15 weight percent chlorine. The catalyst may, if desired, contain a minor amount, that is, from about 0.01 to about 5 weight percent of a Group VIII metal such as platinum, palladium, rhodium or ruthenium. A Group VII metal such as rhenium may also be present in amounts of about 0.01 to 1.0 weight percent. The catalyst employed in the instant process can be prepared by chloriding alumina or a Group VII or Group VIII metal-alumina composite by known methods. Illustratively, the alumina may be contacted with carbon tetrachloride, chloroform, methylene chloride, dichlorodifluoromethane, trichlorobromomethane, thionyl chloride or thiocarbonyl tetrachloride under nonreducing conditions, that is, under inert or oxidizing conditions and where the latter is preferred. Other methods of chloriding known to the art involve contacting the alumina with a combination of chlorine and hydrogen sulfide or an organic compound such as tetrachloroethane, tetrachloroethylene, hexachloroethane, pentachloroethane, hexachloroacetone, hexachloro-1,3-butadiene, hexachloropropanone-2, hexachlorocyclopentadiene, hexachloropropylene, trichloroacryloyl chloride, trichloroacetyl chloride, chloral, ethane, ethylene or propane. In general, any of the known methods for introducing chlorine to alumina by contacting the alumina with the chloriding activator at temperatures of about 200° to about 800° F., most preferably between about 450° and 650° F., can be employed. The amount of chlorinating activator employed should be sufficient to enable the resulting catalyst to contain a chlorine content of about 4 to 15 weight percent.

The catalyst can be provided with additional activity by contacting the chlorided alumina in an oxidizing atmosphere suitably air, oxygen or mixtures containing chlorine at a temperature of between about 700° and 1200° F. and at a pressure of between about 0 and 100 p.s.i.g. Typically, the oxidizing atmosphere is introduced as a flowing gaseous stream at a volumetric flow rate of at least 8 and up to 80 standard cubic feet per hour per pound of catalyst for a period of at least 1 hour and up to about 48 hours. The catalyst following the oxidizing treatment is thereafter contacted with the chloriding activators and conditions mentioned above. Alternately, contacting can be undertaken with aluminum chloride at a temperature of between about 300° and 650° F., preferably 450° and 600° F. and under a pressure of about 0 to 300 p.s.i.g. From about 2 to 40 parts by weight of aluminum chloride per 100 parts by weight of chlorided alumina are employed in the contacting. Under the conditions described herein, the contacting of the chlorided alumina with aluminum chloride in vaporized form provides a further chlorination of the catalyst's surface by reacting therewith. Such additional chlorination with aluminum chloride does not, however, result in the deposition of aluminum chloride onto the catalyst's surface. Instead, by contacting with the vaporized aluminum chloride, the chlorided composite is provided with higher levels of chlorine within the range of about 7 to 15 weight percent. Likewise, treatment by contacting with the chloriding activators provides the higher levels of chlorine to the catalyst. The additional chlorination enables formation of very strong acid sites involving a complex of aluminum and chlorine on the surface of the catalyst and by such means provides the instant process with a highly desirable catalyst.

According to this invention, the self-alkylation process employing the solid chlorided alumina catalyst is conducted at relatively low temperatures. In general, the reaction temperature should be from about 75° F. to 250° F., and preferably between about 100° and about 200° F. Suitable pressures range from about 50 to about 300 p.s.i.g. The process contemplated comprises contacting from about 11 to 150 moles of isobutane per mole of olefin, preferably 20 to 100 moles of isobutane per mole of olefin. The process is suitably conducted at a LHSV of between about 0.5 and 20.0, and the feed is introduced into and through the reaction zone containing the chlorided alumina catalyst. The catalyst is suitably in the form of, for example, 1/16 inch or ⅛ inch extrudates. The catalyst may, however, be employed in other well-known forms, such as pellets, granular compositions or beads.

With respect to the self-alkylation reaction, isobutane and a $C_5$ to $C_9$ olefin are contacted with the catalyst under the self-alkylation conditions described above. Preferably, neat streams of isobutane and olefin are respectively introduced to the reactor. Multiple injection points of olefin are also desirable where the cumulative amount of olefins contacted with isobutane is within the mole ratio set out above. The multiple injection of olefin can be continuously undertaken along the fluid flow in the reactor employing up to 10 injection points, preferably 5 to 10 injection points. Multiple injection is preferred in that it promotes hydrogen transfer from the isobutane to olefin, aids in inhibiting polymerization of the olefin and deters catalyst fouling. Higher olefin contents contacting the catalyst promote polymerization or direct alkylation thereby reducing the amount of desired isobutane self-alkylation.

Individual or mixtures of $C_5$ to $C_9$ olefins may be employed. Preferred olefins are the $C_6$ and $C_7$ olefins with $C_6$ or $C_7$ isoolefins being particularly preferred. Suitable olefins include pentene-1, pentene-2, hexene-1, hexene-2, 4-methylpentene-1, heptene-1, 4-methylhexene-1, cyclohexene, 4-methylcyclohexene, 4-methylheptene-1, 3-methylheptene-2 and 2-methyloctene-1. Combinations of normal, iso- and cycloolefins can also be employed. Preferred olefins include 4-methylpentene-1 and 4-methylcyclohexene.

In another embodiment of our invention, the self-alkylation process described above is integrated with and utilized in combination with an isomerization process. It is contemplated that the self-alkylation reaction will utilize isomerized hydrocarbons containing isobutane derived from the isomerization of isomerizeable hydrocarbons comprising n-butane.

The isomerizeable hydrocarbons employed as the feed to an isomerization reactor comprises n-butane alone or a $C_4$ stream comprising substantial amounts of n-butane. Further, mixtures of isomerizeable hydrocarbons, suitably $C_4$ to $C_6$ hydrocarbons comprising n-butane along with isomerizeable pentanes and hexanes, can be used as the isomerization feedstock. Preferably, the feed to the isomerization reactor consists essentially of n-butane.

More particularly, the isomerizeable hydrocarbon stream comprising n-butane is introduced to an isomerization reactor by passing the stream together with hydrogen to a reactor containing a conventional isomerization catalyst. Any of the typical and well-known isomerization catalysts can be employed including, for example, halogenated supported noble metal compositions, such as chlorided platinum on alumina. Suitable isomerization conditions include temperatures of about 300° to 400° F. and preferably 315° to 350° F., pressures of about 300 to 750 p.s.i.g. and a liquid hourly space velocity (LHSV) of about 0.5 to 10.0. The hydrogen to hydrocarbon mole ratios may vary within a wide range and generally from about 0.05:1 to 5:1 and preferably from about 0.1:1 to 1:1.

In a typical operation, the isomerizeable hydrocarbon feed comprising n-butane is introduced to an isomerization reactor containing a known isomerization catalyst and the reactor is maintained under conventional isomerization conditions of temperature and pressure suitable for isomerizing n-butane to isobutane. The isomerization effluent containing isomerized hydrocarbons is withdrawn from the isomerization vessel and passes to a high pressure separator where gaseous components, predominantly hydrogen, are taken overhead and may be recycled for reintroduction to the isomerization reactor. Where the feed to the isomerization reactor is composed of essentially n-butane, the separated liquid effluent comprising n-butane and isobutane can be introduced directly to the self-alkylation reactor. Alternately, where the isomerizeable hydrocarbon feed is composed of mixtures of, for example, $C_4$ to $C_6$ hydrocarbons, the liquid is withdrawn from the separator and enters a debutanizer from which a butane fraction is taken overhead. The debutanized liquid is withdrawn from the debutanizer and can be treated or recovered according to well-known procedures. For example, it is generally desirable to recover the isopentanes and isohexanes. Low octane components, such as normal pentanes and hexanes, can be recycled for reintroduction to the isomerization vessel. In a like manner, the butane fraction taken overhead can be routed to a deisobutanizer wherein isobutane is taken overhead and routed to the self-alkylation reactor and the bottoms comprising n-butane recycled to the isomerization reactor. Similarly, where the isomerizeable hydrocarbon stream consisted essentially of n-butane, the isomerization effluent can be routed to a deisobutanizer and the stream to the self-alkylation reactor will consist essentially of isobutane. The isomerized isobutane containing stream separated above along with a $C_5$ and higher olefin are introduced to a self-alkylation reactor as described above wherein isobutane is self-alkylated in the presence of a solid catalyst comprising chlorided alumina under self-alkylation conditions.

The effluent from the self-alkylation reactor comprises as product isooctane from the self-alkylation of isobutane and $C_5$ and higher isoparaffins along with n-butane and unconverted isobutane. The $C_4$ components are separated from the self-alkylation effluent, suitably by fractionation, and the $C_4$ fraction can be recycled to the isomerization reactor along with make-up isomerizeable hydrocarbons. Preferably, the $C_4$ components are separated into an n-butane fraction and an isobutane fraction. In this instance, the n-butane fraction is recycled to the isomerization reactor and the isobutane fraction is recycled for reintroduction to the self-alkylation reactor.

The self-alkylation of isobutane and the combined isomerization self-alkylation process described herein provides an alkylate yield rich in $C_5$ to $C_9$ components including a substantial amount of $C_8$ isomers. A by-product provided by the reaction is a paraffin corresponding in carbons to the olefin employed. For example, where the olefin of choice is hexene-1, the alkylate composition will contain $C_6$ components including n-hexane, 2,2-dimethylbutane, 2,3-dimethylbutane and methylpentanes. In addition, when a 1-olefin is charged, the resulting paraffin of comparable carbon content is predominantly in the isoparaffin form. The alkylate composition recoverable from the reaction possesses a high research octane number and the composition is suitable as a gasoline blending component.

In order to more fully illustrate the nature of our invention and the manner of practicing the same, the following examples are presented.

EXAMPLE 1

A feed comprising two weight percent 4-methylpentene-1 in isobutane (mole ratio of isobutane to olefin of 71:1) was introduced to a reactor containing a solid catalyst composed of alumina, 9.5 weight percent chlorine and about 0.6 weight percent platinum under self-alkylation conditions of 110° F., 300 p.s.i.g. and a liquid hourly space velocity of 6.0. The results are summarized in Table I.

EXAMPLE 2

A feed comprising two weight percent 1-hexene in isobutane (mole ratio of isobutane to olefin of 71:1) was introduced to a reactor containing a solid catalyst composed of alumina, 7 weight percent chlorine and about 0.4 weight percent platinum under the self-alkylation conditions described in Example I. The results are summarized in Table I.

EXAMPLE 3

A feed comprising two weight percent 4-methylcyclohexene in isobutane (mole ratio of isobutane to olefin of 81:1) was introduced to a reactor containing a solid catalyst composed of alumina, 7 weight percent chlorine and about 0.4 weight percent platinum under the self-alkylation conditions described in Example I. The results are summarized in Table I.

1 and 2 further provided alkylate compositions having high RON clear and Example 2 demonstrates that the $C_6$ content of the alkylate is predominantly in the iso-$C_6$ form.

EXAMPLE 4

Following the procedure and conditions of Example 2, a feed of two weight percent hexene-1 isobutane was charged into reactors containing respectively the following: eta alumina; gamma alumina; fluorided (7%) eta alumina; and chlorided (2%) eta alumina. No reaction occurred in the presence of the aforementioned materials.

EXAMPLE 5

To an isomerization reactor containing 80 tons of a conventional isomerization catalyst composed of chlorided platinum-alumina having a platinum content of 0.5 weight percent and a chlorine content of 8 weight percent maintained at 340° F. and 500 p.s.i.g. there is introduced 157 barrels of fresh n-butane along with a recycle comprising 410 barrels of n-butane and 433 barrels of isobutane at a hydrogen to hydrocarbon mole ratio of 1:4 (325 SCF of hydrogen per barrel of n-$C_4$ feed) and at a liquid hourly space velocity of 2. The isomerization process effluent is discharged into a high pressure separator maintained at 120° F. and 400 p.s.i.g. where relatively pure hydrogen is separated from the isomerized hydrocarbons (590 barrels of isobutane and 410 barrels of n-butane).

To a self-alkylation reactor containing 80 tons of a solid catalyst composed of alumina, 9.5 weight percent chlorine and about 0.6 weight percent platinum, there is introduced 1,000 barrels per hour of isomerized hydrocarbons (590 barrels of isobutane) and 100 barrels per hour of 4-methylpentene-1 (API Gravity 76.5) are injected continuously to the reactor at 10 points along the fluid flow under self-alkylation conditions including 100° F. and 300 p.s.i.g. The self-alkylation effluent containing 433 barrels of isobutane, 410 barrels of n-butane, 105 barrels of isohexane (API Gravity 82.5) and 125 barrels of isooctane per hour (API Gravity 63.4) is fractionated to separate an overhead $C_4$ stream com-

TABLE I

| Example | 1 | 2 | 3 |
|---|---|---|---|
| OLEFIN | 4-methyl-pentene-1 | hexene-1 | 4-methyl-cyclohexene |
| ALKYLATE YIELD, WT. % | 204 | 270.4 | 94 |
| ALKYLATE YIELD, Wt. % (Theory) | 172 | 172 | 163 |
| ALKYLATE COMPOSITION Wt. % | | | |
| i-$C_5$ | 30.0 | 31.1 | 0.3 |
| $C_6$ | 20.9 | 18.8 | 0.2 |
| $C_7$ | 10.1 | 10.9 | 19.7 |
| $C_8$ | 30.5 | 20.3 | 43.1 |
| $C_{9+}$ | 8.5 | 18.9 | 36.7 |
| TRIMETHYLPENTANE CONTENT, WT. % | 12.5 | 9.7 | 18.2 |
| $C_6$ CONTENT, WT. % | | | |
| n-$C_6$ | — | 4.7 | — |
| 2,2-dimethylbutane + 2,3-dimethylbutane | — | 4.2 | — |
| Methylpentanes | — | 9.9 | — |
| Bromine Number | 0 | 1.1 | — |
| RON Clear | 87.6 | 86.0 | — |

From Table I it will be seen that alkylates containing a substantial octane content were provided in Examples 1–3. Further, Examples 1 and 2 demonstrate that alkylate yields significantly greater than theoretical were obtained. Examples 1 and 3 employing an isoolefin provided the highest octane component content. Examples posed of isobutane and n-butane and the stream is recycled for introduction to the isomerization reactor. A bottoms fraction of 230 barrels of iso-$C_6$ and higher is recovered having a clear RON of 101.

EXAMPLE 6

To an isomerization reactor containing 22 tons of a conventional chlorided platinum-alumina isomerization catalyst having a platinum content of 0.5 weight percent and a chlorine content of 8 weight percent maintained at 340° F. and 500 p.s.i.g. there is introduced 157 barrels of fresh n-butane along with a recycle comprising 110 barrels of n-butane at a hydrogen to hydrocarbon mole ratio of 1:4 (325 SCF of hydrogen per barrel of n-butane) and a liquid hourly space velocity of 2. The isomerization process effluent is discharged into a high pressure separator maintained at 120° F. and 400 p.s.i.g. where relatively pure hydrogen is separated from the isomerized hydrocarbons (157 barrels of isobutane and 110 barrels of n-butane).

To a self-alkylation reactor containing 55 tons of a solid catalyst composed of alumina, 9.5 weight percent chlorine and about 0.6 weight percent platinum, there is introduced 700 barrels per hour of a feed consisting of 267 barrels of isomerized hydrocarbon along with a recycle comprising 433 barrels of isobutane and 100 barrels per hour of 4-methylpentene-1 injected continuously to the reactor at 10 points along the fluid flow under self-alkylation conditions including 100° F. and 300 p.s.i.g. The self-alkylation effluent containing 433 barrels of isobutane, 410 barrels of n-butane, 105 barrels of isohexane and 125 barrels of isooctane per hour is fractionated to separate an overhead $C_4$ stream composed of isobutane and normal butane and a bottoms fraction of 230 barrels containing isohexane and higher having a clear RON of 101. The overhead $C_4$ fraction is introduced to a $C_4$ splitter where 433 barrels of isobutane are removed overhead and recycled for introduction to the self-alkylation reactor. The bottoms (110 barrels of n-butane) are recycled to the isomerization reactor.

We claim:

1. A process for the self-alkylation of isobutane which consists essentially of contacting isobutane and a $C_5$ or higher olefin at a temperature between about 75° and 250° F. with a solid catalyst comprising chlorided alumina, wherein the mole ratio of said isobutane to olefin is from about 11:1 to 150:1 and forming isooctane.

2. A process according to claim 1 wherein said catalyst comprises from about 4.0 to 15.0 weight percent chlorine.

3. A process according to claim 1 wherein said catalyst comprises from about 7.0 to 15.0 weight percent chlorine.

4. A process according to claim 1 wherein said catalyst comprises from 0.01 to 5.0 weight percent of a Group VIII metal.

5. A process according to claim 1 wherein said catalyst comprises from 0.01 to 1.0 weight percent of a Group VII metal.

6. A process according to claim 1 wherein said self-alkylation is undertaken at a temperature of between about 100° and 200° F.

7. A process according to claim 1 wherein the mole ratio of said isobutane to olefin is from about 20:1 to 100:1.

8. A process according to claim 1 wherein said olefin is a $C_5$ to $C_9$ olefin or mixtures thereof.

9. A process according to claim 1 wherein said olefin is a $C_6$ or $C_7$ olefin.

10. A process according to claim 1 wherein said olefin is 4-methylpentene-1.

11. A process according to claim 1 wherein said olefin is hexene-1.

12. A process according to claim 1 wherein said olefin is 4-methylcyclohexene.

13. A process for the self-alkylation of isobutane which comprises:
    (a) contacting hydrogen and a stream comprising n-butane with an isomerization catalyst under isomerization conditions and converting a portion of said n-butane to isobutane;
    (b) separating hydrogen from said isomerized stream of (a);
    (c) contacting said isomerized stream of (b) consisting essentially of isobutane and a $C_5$ and higher olefin with a solid catalyst comprising chlorided alumina at a temperature between about 75 and 250° F., wherein the mole ratio of said isobutane to olefin is from about 11:1 to 150:1 and forming isooctane and $C_5$ and higher isoparaffins; and
    (d) separating said isooctane and $C_5$ and higher isoparaffins from $C_4$ hydrocarbons and recycling said $C_4$ hydrocarbons to (a).

14. A process according to claim 13 wherein isobutane is separated from said $C_4$ hydrocarbons in (d) and where said isobutane is recycled to (c).

15. A process according to claim 13 wherein a portion of said $C_5$ and higher olefin is contacted with said isobutane and introduced to a self-alkylation reactor at a plurality of points.

16. A process according to claim 13 wherein said solid catalyst comprises from about 4.0 to 15.0 weight percent chlorine.

17. A process according to claim 13 wherein said solid catalyst comprises from about 7.0 to 15.0 weight percent chlorine.

18. A process according to claim 13 wherein said solid catalyst comprises from about 0.01 to 5.0 weight percent of a Group VIII metal.

19. A process according to claim 13 wherein step (c) is undertaken at a temperature of between 100° and 200° F.

20. A process according to claim 13 wherein the mole ratio of said isobutane to olefin in step (c) is from about 20:1 to 100:1.

21. A process according to claim 13 wherein said olefin in step (c) is a $C_5$ to $C_9$ olefin or mixtures thereof.

22. A process according to claim 13 wherein said olefin in step (c) is a $C_6$ or $C_7$ olefin.

23. A process according to claim 13 wherein said olefin in step (c) is 4-methylpentene-1.

24. A process according to claim 13 wherein said olefin in step (c) is hexene-1.

25. A process according to claim 13 wherein said olefin in step (c) is 4-methylcyclohexene.

* * * * *